(12) United States Patent
Baddoura

(10) Patent No.: US 7,566,443 B2
(45) Date of Patent: Jul. 28, 2009

(54) METHOD FOR DIAGNOSIS OF CHRONIC ALLOGRAFT REJECTION

(75) Inventor: Fady K. Baddoura, Snyder, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 54 days.

(21) Appl. No.: 11/520,356

(22) Filed: Sep. 13, 2006

(65) Prior Publication Data

US 2007/0059240 A1 Mar. 15, 2007

Related U.S. Application Data

(60) Provisional application No. 60/716,626, filed on Sep. 13, 2005.

(51) Int. Cl.
*A61K 49/00* (2006.01)
*G01N 33/53* (2006.01)
(52) U.S. Cl. .......................... 424/9.1; 435/7.1
(58) Field of Classification Search ............... None
See application file for complete search history.

(56) References Cited

U.S. PATENT DOCUMENTS 6,375,925 B1 * 4/2002 Tsimikas et al. ............ 424/1.49

OTHER PUBLICATIONS

Topplia et al. Endothelial L-selectin ligands are likely to recruit lymphocytes into rejecting human heart transplants. Am J Pathol. Oct. 1999;155(4):1303-10.*
Toogood et al. The immune response following small bowel transplantation: I. An unusual pattern of cytokine expression. Transplantation. Sep. 27, 1996;62(6):851-5.*
Baddoura et al. Lymphoid neogenesis in murine cardiac allografts undergoing chronic rejection. Am J Transplant. Mar. 2005;5(3):510-6.*
Rosen DR. Endothelial ligands for L-selectin: from lymphocyte recirculation to allograft rejection. Am J Pathol. Oct. 1999;155(4):1013-20.*
Kurkijärvi et al. Vascular adhesion protein-1 (VAP-1) mediates lymphocyte-endothelial interactions in chronic kidney rejection. Eur J Immunol. Oct. 2001;31(10):2876-84.*
Licha et al. Optical molecular imaging of lymph nodes using a targeted vascular contrast agent. Journal of Biomedical Optics, vol. 10, issue 4, p. 041205.*
Thaunat et al. Lymphoid neogenesis in chronic rejection: evidence for a local humoral alloimmune response. Proc Natl Acad Sci U S A. Oct. 11, 2005;102(41):14723-8. Epub Sep. 28, 2005.*
Ruddle; Lymphoid Neo-organogenesis: Lymphotoxin's Role in Inflammation and Development; Immunologic Research, 1999, vol. 19(2-3); pp. 119-125.

Hjelmstrom; Lymphoid Neogenesis: *De Novo* Formation of Lymphoid Tissue in Chronic Inflammation through Expression of Homing Chemokines; Journal of Leukocyte Biology, Mar. 2001, vol. 69; pp. 331-339.
Weyand, et al.; Ectopic Lymphoid Organogenesis: A Fast Track for Autoimmunity; American Journal of Pathology, Sep. 2001, vol. 159, No. 3; pp. 787-793.
Drayton, et al.; Ectopic LTαβ Directs Lymphoid Organ Neogenesis with Concomitant Expression of Peripheral Node Addressin and a HEV-restricted Sulfotransferase; J. Exp. Med., May 5, 2003, vol. 197, No. 9; pp. 1153-1163.
Girard, et al.; High Endothelial Venules (HEVs): Specialized Endothelium for Lymphocyte Migration; Immunology Today, 1995, vol. 16, No. 9; pp. 449-457.
Kratz, et al.; Chronic Inflammation Caused by Lymphotoxin is Lymphoid Neogenesis; J. Exp. Med. Apr. 1996, vol. 183; pp. 1461-1472.
Schrama, et al.; Targeting of Lymphotoxin-α to the Tumor Elicits an Efficient Immune Response Associated with Induction of Peripheral Lymphoid-like Tissue; Immunity, Feb. 2001, vol. 14; pp. 111-121.
Yu, et al.; Priming of Naive T Cells Inside Tumors Leads to Eradication of Established Tumors; Nature Immunology, Feb. 2004, vol. 5, No. 2; pp. 141-149.
Corry, et al.; Primarily Vascularized Allografts of Hearts in Mice; Transplantation, 1973, vol. 16, No. 4; pp. 343-350.
Billingham, et al.; A Working Formulation for the Standardization of Nomenclature in the Diagnosis of Heart and Lung Rejection: Heart Rejection Study Group; The Journal of Heart Transplantation, 1990, vol. 9, No. 6; pp. 587-593.
Chalasani, et al.; The Allograft Defines the Type of Rejection (Acute Versus Chronic) in the Face of an Established Effector Immune Response; The Journal of Immunology, 2004, vol. 172; pp. 7813-7820.
Hemmerich, et al.; Sulfation-dependent Recognition of High Endothelial Venules (HEV)-Ligands by L-Selectin and MECA 79, an Adhesion-blocking Monoclonal Antibody; The Journal of Experimental Medicine, Dec. 1994, vol. 180; pp. 2219-2226.
Licha K, et al. Optical molecular imaging of lymph nodes using a targeted vascular contrast agent. J. Biomed. Opt. (2005) vol. 10: p. 41205 (Abstract).

* cited by examiner

*Primary Examiner*—Maher M Haddad
(74) *Attorney, Agent, or Firm*—Hodgson Russ LLP

(57) ABSTRACT

The present invention provides a method for the diagnosis of chronic rejection in allografts. The method comprises identification of tertiary lymphoid organs (TLO) in the transplanted organs as a marker of chronic rejection by immunohistochemical detection for the presence of specific TLO antigens in biopsy samples or by radiographic imaging of radiolabeled antibodies to specific TLO antigens. In one embodiment, the presence of TLO is detected by the intravenous administration of a radiolabeled antibody to PNAd followed by radiographic imaging to determine the presence or absence of PNAd in the transplanted organ. The presence of PNAd in the transplanted organ is taken as an indication of chronic rejection.

1 Claim, 2 Drawing Sheets

METHOD FOR DIAGNOSIS OF CHRONIC ALLOGRAFT REJECTION

This application claims priority to U.S. provisional application No. 60/716,626, filed on Sep. 13, 2005, the disclosure of which is incorporated herein by reference.

FIELD OF THE INVENTION

The invention generally relates to organ transplantation and more particularly provides a method for the accurate and early diagnosis of chronic rejection of transplanted organs.

BACKGROUND OF THE INVENTION

Transplantation is the treatment of choice for many patients with organ failure such as end-stage renal, hepatic or pulmonary disease, refractory heart failure, and various other conditions. Despite a considerable advancement in therapeutic modalities, allograft rejection continues to pose a serious threat to the overall survival of transplant patients. Chronic rejection remains the most important cause of graft loss with a prevalence rate as high as 80% in some renal transplantation series, thus limiting the overall success of solid organ transplantation. The mechanisms that prevent permanent allograft acceptance are uncertain and have not been systematically investigated. For these reasons, current clinical strategies are focused primarily on prevention and early diagnosis since there are no effective therapies that permanently safeguard the allograft against rejection in the absence of continuous, potentially harmful, immunosuppression.

Currently, chronic rejection of transplanted organs is diagnosed by pathological analysis, which requires a biopsy of the allograft. This procedure is invasive by nature with potential complications such as bleeding, infection or organ perforation. It is a costly multidisciplinary procedure involving surgeons, anesthesiologists, Operating Room personnel, histotechnologists and pathologists. It is subject to sampling error and the diagnosis may be overlooked or misinterpreted by the examining pathologist due to very subtle or non-specific pathological changes as described in the literature. Indeed, the pathological criteria used to establish the diagnosis of chronic rejection including thickening of intimal layer with luminal narrowing and fibrosis of the interstitium are non-specific findings that may be seen in other diseases or conditions such as diabetes, hypertension or aging, which may lead to false positive results. In addition, these changes can be very minimal and focal in nature so that they may be overlooked and completely missed, thus reducing the sensitivity of this technique particularly in early detection. These overall limitations are due to the absence of a specific diagnostic marker of chronic rejection. Therefore, there is a continuing need in the field of organ transplantation to identify markers that can be used for the accurate and early diagnosis of chronic allograft rejection.

SUMMARY OF THE INVENTION

The present invention provides a specific method for the diagnosis of chronic rejection in allografts. The method comprises the identification of tertiary lymphoid organs (TLO) in the transplanted organs as a marker of chronic rejection. TLO can be identified by detecting one or more of their specific constituents.

In one embodiment, the presence of TLO is detected in tissue samples obtained by biopsy of the transplanted organ by the use of an antibody to a TLO antigen (such as peripheral node addressin or PNAd).

In another (and preferred) embodiment, by the intravenous administration of a radiolabeled antibody to PNAd and carrying out radiographic imaging to determine the presence or absence of PNAd in the transplanted organ. The presence of PNAd in the transplanted organ is therefore indicative of chronic rejection.

DESCRIPTION OF THE INVENTION

Figure 1:
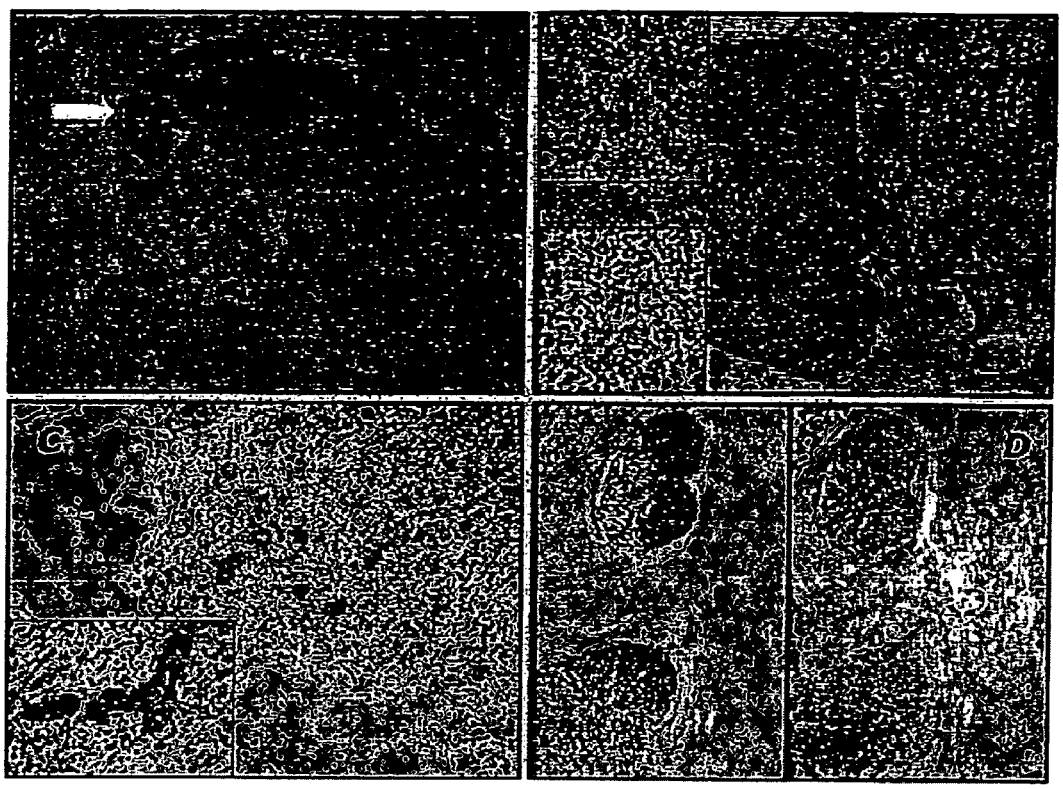
FIG. 1: Tertiary lymphoid organs (TLO) in murine cardiac allografts undergoing combined acute and chronic rejection. (A) lymph node-like structures (white arrow) in the pericardium of a cardiac allograft rejected 174 days after transplantation (H&E, 100×). (B) Intracardiac lymph-node-like structure in an allograft rejected 185 days after transplantation (H&E, 100×). Red arrows point to distinct lymphoid follicles with germinal centers and outer mantle zones. Top inset, pale staining sinuses (black arrows) surrounding dense lymphocyte zones (H&E, 200×). Bottom inset, high endothelial venule (HEV)-like vessel (white arrows) with plump endothelial lining that occupies the lumen (H&E, 400×), (C) HEV-like vessels within TLO are intensely positive (brown color) for peripheral node addressin (PNAd) in a cardiac allograft harvested 187 days after transplantation (MECA-79, 100×). Inset, high power view showing PNAd$^+$ HEV with the stronger staining more evident on the luminal side of the endothelium (red arrows) (MECA-79, 400×). (D) Distinct compartmentalization of B cells (left panel) and T cells (right panel) within TLO follicles in a cardiac allograft harvested 180 days after transplantation (B220/anti-CD3, 100×).

Lymphoid neogenesis is the process by which ectopic lymphoid accumulations that resemble peripheral lymph nodes develop in nonlymphoid tissues (1-3). Such ectopic lymphoid accumulations, also known as tertiary lymphoid organs (TLO), arise in the course of chronic inflammation caused by either autoimmunity or microbial infection. In humans, TLO have been described in the thyroid gland (Hashimoto's thyroiditis), central nervous system (multiple sclerosis), thymus (myasthenia gravis), joints (rheumatoid arthritis), salivary glands (Sjogren's syndrome), gastric mucosa (*Helicobacter pylori* infection), liver (primary sclerosing cholangitis and chronic hepatitis C) and skin (*Borrelia burgdorferi* infection) (1-3).

TLO contain elements of chronic inflammation as well as secondary lymphoid organs, specifically peripheral lymph nodes (4). Structural elements reminiscent of lymph node architecture that define TLO are: (a) high endothelial venules (HEV); (b) discrete naïve T- and B-cell accumulations (c) antigen-presenting cells and follicular dendritic cell (FDC) networks and (d) in some cases, germinal centers. HEV derive their name from the cuboidal high-walled configuration of their endothelial cells and are uniquely found in the T-cell zones of secondary lymphoid tissues (5). As in peripheral lymph nodes, HEV present in TLO express peripheral lymph node addressin (PNAd) and mucosal addressin cell adhesion molecule (MAdCAM-1). PNAd and MAdCAM-1 mediate the extravasation of naïve lymphocytes by binding to L-selectin (CD62L) and $\alpha_4\beta_7$ integrin, respectively (5). Several reports have provided evidence that TLO support naïve T-cell activation. Kratz et al. found that TLO induced by ectopic production of lymphotoxin-$\alpha$ (LT$\alpha$) in the kidney acquire IgM- and IgG-producing lymphocytes following immunization with sheep RBC (6). Similarly, induction of TLO elements, for example PNAd$^+$ HEV, inside tumors leads to enhanced eradication of the tumor cells (7, 8). Therefore, it is postulated that lymphoid neogenesis is beneficial to the host in tumors or infection by setting up local sites of antigen presentation but may be deleterious in autoimmunity by establishing lymphoid tissues in close proximity to autoantigens (3).

In this invention, we demonstrate the presence of TLO in murine allografts undergoing rejection and their complete absence in both stable allografts and syngeneic grafts by virtue of histologic morphology, B-cell and T-cell compartmentalization and the antigenic expression of PNAd on the surface of high endothelial venules (HEV)-like vessels. We also show that in the mouse, intragraft tertiary lymphoid organs generate both effector and immune responses that lead to rejection. These findings strongly suggest that TLO can initiate and perpetuate immune responses within the graft. Furthermore, in a study involving a limited number of human biopsy samples obtained from chronically rejected transplanted organs, TLO were observed in chronic rejection and not in stable allografts. Based on these findings, the present invention utilizes the concept that the HEV bound L-selectin ligand PNAd is a highly specific and sensitive marker for chronic rejection. In one embodiment, PNAd can be detected in biopsy specimens by immunohistochemistry. For this type of detection, a sample of the transplanted organ tissue can be obtained by routine techniques and PNAd antibodies can be used to determine the absence or presence of PNAd. In a preferred embodiment, radiolabeled anti-PNAd antibodies can be administered to the individual followed by radiographic imaging (i.e., obtaining a scintillographic image). In the radiogaphic method, surgical sampling errors and pitfalls in diagnosis due to pathological misinterpretation are obviated and replaced by a more accurate and objective test that is also faster (same day diagnosis), safer, and less costly.

The present method takes advantage of the presence of specific markers that are structural constituents of TLO and, by the same token, indicative of their presence. PNAd is provided as an example of such a marker, but any other structural or antigenic constituent specific to lymphoid organs can be used as well. Therefore, in a preferred embodiment of this invention, a detectably labeled molecule having a specific affinity for PNAd is administered to an individual who has undergone organ transplantation. One example of such a molecule is a radiolabeled antibody for PNAd. PNAd, an L-selectin ligand is a sulfo-sialyl Lewis$^x$ determinant common to several glycoproteins (GlyCAM-1, CD34, podocalyxin and MAdCAM-1). The interaction of L-selectin on naïve lymphocytes with sulfated glycoprotein ligands on HEV results in lymphocyte rolling which represents the initial step in lymphocyte homing, thus leading to extravasation of naïve B cells and T cells into lymph nodes. Sulfation of these glycoproteins is catalyzed by a HEV-specific sulfotransferase HEC-6ST (also known as GlcNAc6ST-2) and is necessary for their luminal expression on endothelial cells where they are most likely to interact with circulating lymphocytes. Example of detectable labels used in imaging include, but are not limited to, compounds with relatively large atoms, such as gold, iridium, technetium, barium, thallium, iodine, and their isotopes.

Any antibody that specifically binds to PNAd can be used for the diagnosis of chronic rejection. Commercially available antibodies can be used or new antibodies can be generated by standard techniques. For example, a purified monoclonal antibody against PNAd, clone MECA-79, is commercially available from BD Pharmingen™ (10975 Torreyana Road, San Diego, Calif. 92121, Tel: 877-232-8995) and ATCC™ (American Type Culture Collection (ATCC), P.O. Box 1549, Manassas, Va. 20108, Tel: 703-365-2700), both tested to work in murine and human tissues. MECA-79 recognizes sulfated carbohydrate epitopes (6-sulfo sialyl-Lewis$^x$ and sulfated lactosamine) of peripheral lymph node addressing, blocks L-selectin dependent lymphocyte homing to lymph nodes, and reacts specifically with its antigen in solutions and tissue sections (Hemmerich et al., 1994, Journal of Experimental Medicine, 180:2219-2226). In addition, an anti-human GlcNAc6ST-2 antibody was recently developed by some investigators and was shown to parallel the localization of MECA-79 in human tissues (Pablos et al., 2005, BMC Immunology, 6:6). Those skilled in the art will recognize that other antibodies which recognize the same epitope as PNAd as MECA-79 or anti-GlcNAc6ST-2, or any other epitope of PNAd can be used. Further, antigen binding fragments of such antibodies, such as including F(ab')$_2$, Fab', Fab, Fv, single chain Fv, Fd' and Fd fragments and derivatives of single chain Fv, can also be used.

The in vivo use of anti-PNAd (radiolabeled Peripheral Node Addressin antibodies) radiographic imaging of transplanted organs is expected to solve the problems of current methodologies by virtue of being relatively safe with a reduced cost of health care and, more importantly, a highly specific (100%) and sensitive objective technique that visualizes all the vasculatures in the transplanted organ and exceed the diagnostic usefulness of routine pathological examination of a random biopsy specimen. It would also insure earlier detection of rejection through visualization of the entire allograft. Alternatively, biopsy sample of transplanted organs may also be tested immunohistochemically for the presence of PNAd in order to establish the diagnosis of chronic rejection when radiographic means are unavailable.

In the practice of the invention, detectably labeled affinity molecules (such as radiolabeled anti-human PNAd antibody) are injected under radiographic guidance into the main arterial supply of the transplanted allograft. Dosage and administration are comparable to currently established radiographic diagnostic techniques in Nuclear Medicine, which are typically low dose-pharmaceuticals that are cleared from the body in a short period of time with no significant side effect. In a typical scenario, transplant recipients are injected with radiolabeled antibodies (such as technetium-99m) on day one. Radiographic image is taken on second day to allow sufficient time for the dye to distribute uniformly (i.e., bind and equilibrate). In a normal setting with no evidence of rejection, the vessels of the allograft should not carry PNAd ligands on their endothelial surfaces and, therefore, radiographic imaging of the organ is expected to be negative. On the other hand, in instances of chronic rejection were HEV-like vessels expressing PNAd on their luminal surfaces are formed, binding of radiolabeled antibody to PNAd ligands is expected to occur, leading to a positive radiographic scan. The latter will visualize the entire organ and detect focal or infinitesimal amount of PNAd, thus establishing the diagnosis of chronic rejection even in its earliest stage, likely to be missed in a random biopsy specimen. All patients who are recipient of organ transplantation are at risk of developing chronic rejection, and therefore all can be tested several months to a year after initial transplantation, once yearly thereafter, and any time chronic rejection is suspected on clinical grounds. The method of the present invention can be used for identifying chronic rejection of all solid organ transplants such as heart, liver, lung, kidney, pancreas as well as skin transplants.

The immunohistochemical method for the detection of PNAd in allograft tissue sections (using MECA-79 as an example of anti-PNAd antibody) and therefore establishing the diagnosis of chronic rejection has been established and shown to work in humans and mice undergoing chronic rejection as described elsewhere in this application.

The utilization of anti-PNAd radiographic imaging takes advantage of an objective marker of chronic rejection that is 100% specific and highly sensitive. Other advantages include: Subjective pathological interpretation and sampling error are virtually eliminated by this technology, obviating diagnostic errors and delays; the technique is relatively safe under radiographic guidance and eliminates all potential complications associated with organ biopsy such as bleeding, infection and organ perforation; and significantly less cost is involved using a single specialty (Nuclear Medicine) as opposed to multiple specialties including Surgery, Anesthesiology, Nursing and Pathology.

The following examples are provided to further describe the invention. These examples are intended to be illustrative and should not be construed to be limiting in any way.

EXAMPLE 1

This example describes analysis in a large series of murine cardiac allograft tissues for the presence of lymph-node-like structures. We report here that classical TLO or PNAd+ HEV without organized lymphoid accumulations occur at a significant frequency in murine heart transplants. Importantly, lymphoid neogenesis was observed predominantly in association with chronic allograft rejection but to a much lesser extent with acute rejection.

Materials and Methods

Tissue Samples

Cardiac tissue from all mice that received heart transplants in our laboratories between January 1999 and December 2003 were included in this study. A total of 332 specimens (312 allografts, 7 syngeneic grafts and 13 native hearts) were identified. Pertinent clinical information (donor and recipient strains, type of immunosuppression, type of adoptive cell transfer, time to allograft harvest post transplantation and condition of allograft at time of harvest) as well as archived pathological material including B5/formalin-fixed paraffin-embedded tissue blocks and slide sections were retrieved. Surgical procedures including heterotopic heart transplantation have been described previously (9). Cardiac grafts were harvested either because they ceased to contract (clinical rejection) or at a variable time point (usually>100 days after transplantation) if they continued to function.

Routine Histology

Routine Hematoxylin & Eosin (H&E), Masson-Trichrome (MT) and Verhoess Van Giesen (Elastin)-stained slide sections obtained from all 332 heart specimens were reviewed by light microscopy and examined for the presence of rejection and lymph-node-like structures. Rejection was graded according to the Working Formulation of the International Society for Heart Transplantation (ISHT) (10). The diagnosis of chronic rejection was made if vasculopathy characterized by intimal thickening was present (11). The structural criteria used for identifying TLO were: (a) intracardiac or pericardial lymphoid aggregates that resemble lymph nodes; (b) presence of distinct T- and B-cell zones within these lymphoid aggregates; (c) presence of HEV-like blood vessels with plump endothelial linings within these aggregates; and (d) expression of PNAd on the luminal surface of HEVs (12).

Antibodies

Tissue sections prepared from all 332 paraffin tissue blocks were immunostained using a battery of monoclonal antibodies against T cells (anti-CD3), B cells (anti-CD45R/B220) and PNAd (MECA-79). These antibodies were purchased from Serotec (Serotec USA Inc., Raleigh, N.C.; anti-CD3) and BD Biosciences (BD Biosciences/pharmingen, San Diego, Calif.; anti-CD45R/B220 and MECA-79). The MECA-79 antibody recognizes sulfated carbohydrate epitopes (6-sulfo sialyl-Lewis$^x$ and sulfated lactosamine) of PNAds (GlyCAM-1, CD34, podocalyxin or MAdCAM-1), blocks L-selectin-dependent lymphocyte homing to murine lymph nodes, and reacts specifically with its antigen in formalin-fixed, paraffin-embedded sections (12).

Immunohistochemistry

Deparaffinized and rehydrated 4 µm sections were mounted onto Snowcoat X-tra™ glass slides (Surgipath™ Medical Industries, Inc., Richmond, Ill.). After blocking endogenous peroxidase activity for 15 min in a 3% $H_2O_2$ solution, microwave antigen retrieval was performed using an EDTA solution at pH=8 for 8 min (anti-CD3) or a 1:10 Antigen Retrieval Citra solution (Biogenex, laboratories, Inc., San Ramon, Calif.) at pH=6 for 6 min (anti-CD45R/B220 and MECA-79). Sections were incubated for 50-60 min at room temperature (RT) with primary antibody diluted at 1:100 (anti-CD3 at 1000 µg/mL), 1:30 (anti-CD45R/B220 at 62.5 µg/mL) and 1:20 (MECA-79 at 125 µg/mL) in a 1:1 PBS and 1% milk solution at pH=7.4. Biotinylated species-specific anti-rat IgG secondary antibodies (Vector Laboratories Inc., Burlingame, Calif.) were diluted 1:100 in PBS/milk solution and incubated on sections for 30 min at RT. Slides were treated with a streptavidin-peroxidase reagent (Signet Laboratories Inc., Dedham, Mass.) for 25 min at RT. Enzymatic activity was detected using a diaminobenzidine (DAB) solution (Zymed Laboratories Inc., South San Francisco, Calif.). In all experiments, species-specific isotype-matched irrelevant antibody was used as a negative control. Normal murine peripheral lymph node tissue sections were utilized as positive controls. All sections were counterstained with Hematoxylin, mounted in Acrytol Mounting Medium (Surgipath®) and coverslipped before light microscopic examination. Pathological examination was blinded vis-à-vis specimen identification in all cases. Findings were subsequently correlated with the corresponding clinical parameters and tabulated.

Results

Lymphoid Neogenesis Occurs in Murine Cardiac Allografts

Of the 319 murine cardiac grafts (312 allografts and 7 syngeneic grafts) examined, 78 exhibited histological evidence of lymphoid neogenesis either in the form of organized lymphoid accumulations with morphological and immunohistochemical features of TLO (n=34), or PNAd$^+$ HEV without organized lymphoid accumulations (n=44). Lymphoid neogenesis was not observed in any of the syngeneic grafts or in 13 native hearts removed from transplant recipients at the time of graft harvest. Among the cardiac allografts that had TLO, lymphoid structures that closely resemble peripheral lymph nodes were noted in 30 samples (FIG. 1A, 1B) but were somewhat disorganized in the remaining four. The location of the TLO was either pericardial (FIG. 1A), subpericardial involving the outer myocardial layer, or intramyocardial (FIG. 1B). Like peripheral lymph nodes, intragraft TLO were characterized by the presence of distinct lymphoid follicles, germinal centers and blood vessels with plump endothelial cells indicative of HEV (FIG. 1B). These findings were observed in all 34 samples. In addition, structures similar to lymph node sinuses were identified in 21 samples (FIG. 1B, top inset). Immunostaining with MECA-79 antibody revealed strong abluminal and luminal endothelial expression of PNAd in the HEV-like blood vessels within the lymphoid aggregates in all allografts that had TLO (FIG. 1C). Occasional venules or capillaries outside the TLO also showed strong luminal PNAd expression. These were present in minimally inflamed myocardium, fibrotic myocardium or in pericardial tissues. Immunohistochemical analysis using antibodies against T cells (anti-CD3) or B cells (anti-CD45R/B220) revealed T- and B-cell aggregates compartmentalized into distinct zones in all TLO samples (FIG. 1D). A variable admixture of plasma cells, stromal cells and histiocytic cells was also present within the TLO.

Figure 2:
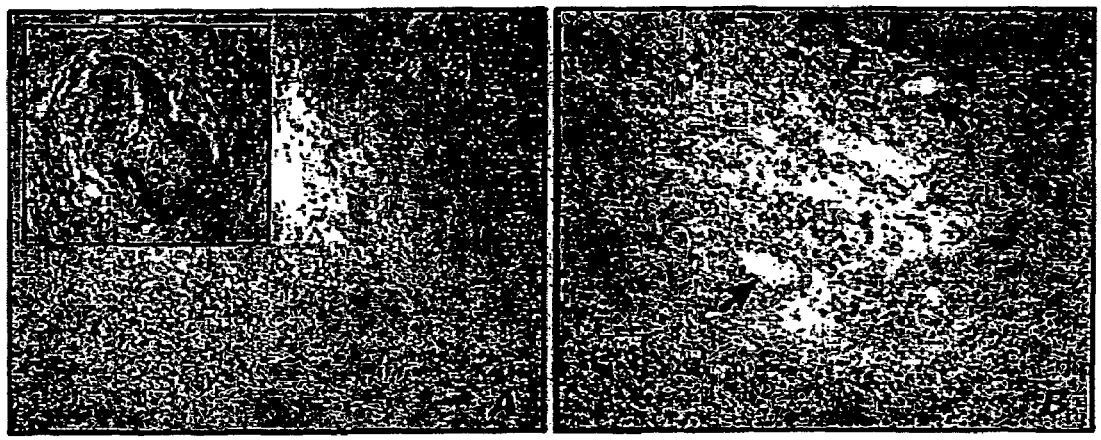
FIG. 2: Peripheral node addressin (PNAd)-expressing vessels without organized lymphoid accumulations in a murine cardiac allograft undergoing combined acute and chronic rejection. (A) Extensive PNAd expression in myocardial vessels surrounded by disorganized inflammatory cell infiltrate (MECA-79, 100×). Inset, small artery showing concentric intimal thickening characteristic of chronic rejection along with PNAd expression on the luminal endothelial surface (MECA-79, 400×). Allograft was harvested 54 days after transplantation. (B) Allograft undergoing severe acute rejection 10 days after transplantation but lacking PNAd$^+$ vessels is shown as negative control (MECA-79, 200×).

We also observed PNAd$^+$ HEV-like vessels within lymphoid infiltrates in 44 additional cardiac allografts. The lymphoid infiltrates in these cases, however, were disorganized and did not segregate into distinct T- and B-cell zones. The extent of PNAd expression was variable, ranging from rare PNAd$^+$ intracardiac or pericardial vessels to diffuse involvement of nearly all small blood vessels within the myocardium (FIG. 2). In summary, lymphoid aggregates found in 78 of the cardiac allografts examined were indicative of lymphoid neogenesis because they either had the morphological and immunohistochemical characteristics of TLO or were associated with PNAd$^+$ HEV surrounded by nonorganized lymphoid infiltrates.

Characteristics of Recipient Mice in which Lymphoid Neogenesis was Observed

Allografts exhibiting lymphoid neogenesis were obtained from a heterogeneous group of mice that had received either fully MHC-mismatched or minor histocompatibility-mismatched allografts (Table 1). The immunologic status of the recipient mice ranged from normal (immunocompetent mice that did not receive immunosuppression) (18%) to either severely immunodeficient (T-cell-deficient or alymphoplastic) (35%) or immunosuppressed mice (47%) (Table 1). In the severely immunodeficient group (n=28), lymphoid neogenesis was observed after wildtype T cells were transferred to the recipient except for two cases where PNAd$^+$ vessels were observed in the absence of adoptive T-cell transfer. Immunodeficient mice were not completely B-cell-deficient to start with, and the transferred T-cell population included contaminating B cells (purity of T cells was approximately 85%). In the immunosuppressed group, the predominant pharmacological agent used was CTLA4-Ig administered either alone or in combination with anti-CD40L, anti-common cytokine receptor γ-chain or anti-IL-2R antibodies. Table 1 provides a comparison between mice that harbored allografts exhibiting lymphoid neogenesis and those whose allografts did not develop either TLO or PNAd$^+$ vessels. Of note is that time to graft harvest tended to be longer in the lymphoid neogenesis group; however, significant overlap between the two groups was present.

Lymphoid Neogenesis is Invariably Associated with Rejection

All examples of lymphoid neogenesis identified in our study were associated with rejection of the transplanted heart. Rejection was clinically evident (absence of heart contractions at the time of harvest) in 18 out of 34 allografts that had TLO (mean survival=85 days, median survival=44 days, range=13-187 days), while the remaining 18 allografts were beating and contracting at the time of harvest (mean and median harvest time=145 and 180 days, respectively; range=56-194 days post transplantation). Histological evidence of rejection, however, was present in all 34 allografts (Table 2). The most common histological finding associated with TLO was a mixture of acute and chronic rejection (79%) followed by predominantly chronic (12%) and predominantly acute rejection (9%). Similarly, all 44 allografts that exhibited PNAd$^+$ vessels without organized lymphoid aggregates had evidence of rejection (Table 2). Clinical rejection occurred in 22 animals (mean survival=67 days, median survival=54 days, range=5-195 days), while the remaining 22 allografts were still beating and contracting at the time of harvest (mean and median harvest time=125 and 100 days, respectively; range=60-189 days post transplantation). On histological examination, mixed acute and chronic rejection was again the most common finding (68%). In contrast, chronic rejection was an uncommon finding in allografts that were free of lymphoid neogenesis. Only 8% of such grafts had histopathologic changes of chronic rejection while 71% had acute rejection. Although the majority of allografts with lymphoid neogenesis failed or were harvested at a late time point after transplantation (median=93 days), PNAd$^+$ HEV or TLO were already present in some instances as early as 5 and 13 days, respectively. Therefore, our data indicate that lymphoid neogenesis in murine cardiac allografts is invariably associated with rejection and can occur either early or late after transplantation. Moreover, histopathologic findings of chronic rejection were present in the majority of allografts that displayed either TLO or PNAd$^+$ HEV but were rare in allografts that had no evidence of lymphoid neogenesis.

Lymphoid Neogenesis Correlates with Chronic Rejection

Figure 3:
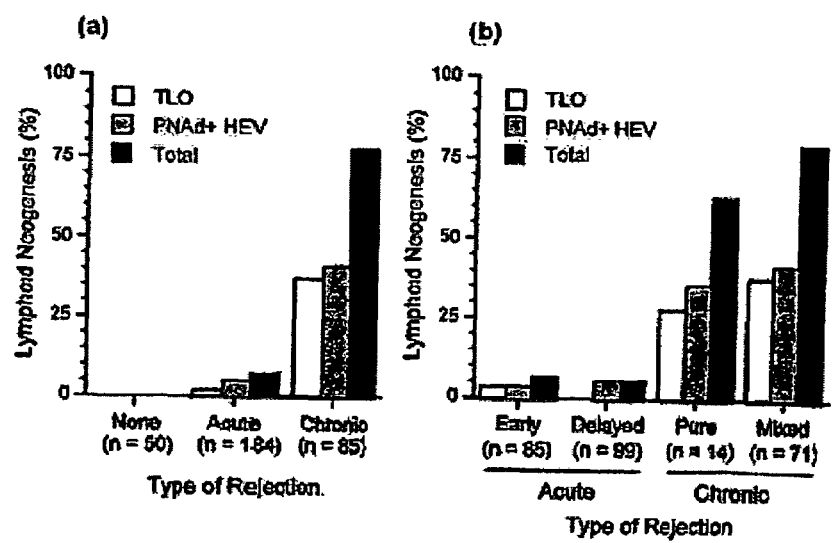
FIG. 3: Prevalence of lymphoid neogenesis according to type of rejection. (A) Prevalence of lymphoid neogenesis (TLO, PNAd$^+$ vessels without organized lymphoid accumulations, or either) in murine cardiac allografts without histological evidence of rejection, and in those with acute or chronic rejection (the former were all 'pure' acute rejection while the latter included either 'pure' chronic rejection or mixed chronic and acute rejection). (B) Prevalence of lymphoid neogenesis in murine cardiac allografts that underwent either early (<21 days post transplantation) or delayed (>21 days post transplantation) acute rejection, and in those that had evidence of either 'pure' chronic rejection or mixed chronic and acute rejection.

The data presented so far suggest that a relationship may exist between lymphoid neogenesis and chronic rejection. To investigate this possibility further, we calculated the prevalence of either TLO or PNAd$^+$ HEV in cardiac allografts classified according to histopathologic type of rejection. As shown in FIG. 3A, lymphoid neogenesis was not observed in the absence of rejection. On the other hand, lymphoid neogenesis occurred in only 7% of allografts undergoing primarily acute rejection and in 78% of allografts that had evidence of chronic rejection. The apparent correlation between lymphoid neogenesis and chronic rejection in the latter group could have resulted from confounding variables such as time after transplantation (since both lymphoid neogenesis and chronic rejection may become more prevalent as allografts survive longer) or the concomitant presence of acute rejection. To rule out these possibilities, we subdivided the allografts undergoing primarily acute rejection into early (≦21 days post transplantation) and delayed (>21 days post transplantation) and the chronic rejection group into pure chronic and mixed chronic plus acute rejection. As shown in FIG. 3B, lymphoid neogenesis occurred at a very low rate in the acute rejection subgroups irrespective of whether rejection was early or delayed (7% and 6%, respectively), but at much higher rates in both the pure and mixed chronic rejection subgroups (64% and 80%, respectively). Of note is that time to graft harvest in the delayed acute rejection group (mean±SD=77±53 days; median=54 days) was not statistically different from that in the chronic rejection group (mean±SD=116±56 days; median=95 days) despite a tendency toward earlier rejection in the former group (p>0.05 by t-test). These data indicate that lymphoid neogenesis correlates with chronic rejection. This correlation could not be attributed to confounding variables such as time elapsed since transplantation or the concomitant presence of acute rejection.

TABLE 1

Graft and recipient characteristics

| Graft or recipient characteristic | Lymphoid neogenesis present (n = 78) (%) | Lymphoid neogenesis absent (n = 241) (%) |
| --- | --- | --- |
| Syngeneic graft | 0 (0%) | 7 (3%) |
| fully allogeneic graft | 70 (90%) | 212 (88%) |
| Minor histocompatibility mismatched graft | 8 (10%) | 22 (9%) |
| Immunodeficient recipient[a] | 27 (35%) | 136 (56%) |
| Immunosuppression administered | 37 (47%) | 87 (36%) |
| Time to graft harvest[b] (mean ± SD) | 104 ± 65 days Median = 93 days (range = 5-195) | 54 ± 50 days Median = 28 days (range = 2-220) |

[a]T-cell-deficient or alymphoplastic;
[b]Cardiac grafts were harvested either because they ceased to contract (clinical rejection) or at a variable time point after transplantation (usually >100 days) if they continued to function.

TABLE 2

Relationship between lymphoid neogenesis and type of rejection

| | Type of lymphoid neogenesis Number (%) | | |
| --- | --- | --- | --- |
| Type of rejection | TLO (n = 34) | PNAd+ HEV (n = 44) | None (n − 241) |
| None | 0 (0%) | 0 (0%) | 50 (21%) |
| Acute | 3 (9%) | 9 (21%) | 172 (71%) |
| Chronic | 4 (12%) | 5 (11%) | 5 (2%) |
| Chronic + acute | 27 (79%) | 30 (68%) | 14 (6%) |

EXAMPLE 2

This example demonstrates that TLO can generate productive alloimmune responses in a mouse that otherwise lacks all secondary lymphoid tissues.

Methods: Skin from RIP-LTα and/or wt donors was transplanted to aly/aly-spleen mice. RIP-LTα mice express LTα under control of the insulin promoter leading to the formation of TLO in the pancreas, kidneys and skin. aly/aly-spleen recipients are devoid of secondary lymphoid tissues and do not reject allografts. Therefore, the only lymph nodes (LN)-like tissue present in this system is confined to the RIP-LTα graft.

Results: Allogeneic (H-$2^{b,d}$) wt skin transplanted to aly/aly-spleen (H-$2^b$) recipients was accepted indefinitely (>200 days, n=6). In contrast, allogeneic RIP-LTα skin (H-$2^{b,d}$), which contains TLO, was acutely rejected (MST=18 days, n=12). Control syngeneic RIP-LTα skin grafts were not rejected (>200 days, n=12). To further test whether intragraft TLO generate an effector immune response, allogeneic wt and RIP-LTα skin were transplanted simultaneously to aly/aly-spleen mice. Both allografts were rejected with the same tempo (MST=52 days, n=6), while wt skin transplanted alone was not. To investigate whether intragraft TLO generate immunologic memory, wt allogeneic skin was transplanted 60 days after aly/aly-spleen mice rejected RIP-LTα allografts. In this case, wt allografts were promptly rejected (MST=16 days, n=6), consistent with a memory recall response. Finally, we tested whether TLO can function as lymph nodes by transplanting syngeneic RIP-LTα skin to aly/aly-spleen mice and, 60 days later, wt skin allografts were transplanted to the same mice. The wt skin was rejected (MST=35 days, n=2), suggesting that the RIP-LTα graft initiated an alloimmune response.

These results show that intragraft TLO generate both effector and immune responses that lead to rejection. This suggests that TLO can initiate or perpetrate immune responses within the graft.

While the above invention has been described through specific examples, routine modifications will be apparent to those skilled in the art and such modifications are intended to be within the scope of this invention.

REFERENCES

1. Ruddle N. Lymphoid neo-organogenesis: Lymphotoxin's role in inflammation and development. *Immunol Res* 1999; 19: 119-125.
2. Hjelmstrom P. Lymphoid neogenesis: De novo formation of lymphoid tissue in chronic inflammation through expression of homing chemokines. *J Leukoc Biol* 2001; 69: 331-339.
3. Weyand C, Kurtin P, Goronzy J. Ectopic lymphoid organogenesis: A fast track for autoimmunity. *Am J Pathol* 2001; 159: 787-793.
4. Drayton D, Ying X, Lee J, Lesslauer W, Ruddle N. Ectopic LTab directs lymphoid organ neogenesis with concomitant expression of peripheral node addressin and a HEV-restricted sulfotransferase. *J Exp Med* 2003; 197: 1153-1163.
5. Girard J, Springer T. High endothelial venules (HEVs): Specialized endothelium for lymphocyte migration. *Immunol Today* 1995; 16: 449-457.
6. Kratz A, Campos-Neto A, Hanson M, Ruddle N. Chronic inflammation caused by lymphotoxin is lymphoid neogenesis. *J Exp Med* 1996; 183: 1461-1472.
7. Schrama D, thor Straten P, Fischer W et al. Targeting lymphotoxin-a to the tumor elicits an efficient immune response associated with induction of peripheral lymphoid-like tissue. *Immunity* 2001; 14: 111-121.
8. Yu P, Lee Y, Liu W et al. Priming of naive T cells inside tumors leads to eradication of established tumors. *Nat Immunol* 2004; 5: 141-149.
9. Corry R J, Winn H J, Russel P S. Primarily vascularized allografts of hearts in mice: The role of H-2D, H-2K, and non H-2 antigens. *Transplantation* 1973; 16: 343-350.
10. Billingham M E, Cary N R B, Hammond M E et al. A working formulation for the standardization of nomenclature in the diagnosis of heart and lung rejection: Heart rejection study group. *J Heart Transplant* 1990; 9: 587-593.

11. Chalasani G, Li Q, Konieczny B et al. The allograft defines the type of rejection (acute versus chronic) in the face of an established effector immune response. *J Immunol* 2004; 172: 7813-7820.

12. Hemmerich S, Butcher E, Rosen S. Sulfation-dependent recognition of high endothelial venules (HEV)-ligands by L-selectin and MECA 79, an adhesion-blocking monoclonal antibody. *J Exp Med* 1994; 180: 2219-2226.

The invention claimed is:

1. A method for diagnosing chronic rejection of a transplanted heart in an individual comprising the steps of:

a) administering a radiolabeled MECA-79 antibody into the vasculature of a transplanted heart;

b) allowing sufficient time for the radiolabeled MECA-79 antibody to distribute in the transplanted heart; and c) obtaining a radiographic image distribution of the radiolabeled MECA-79 antibody in the transplanted heart to determine the presence or absence of radiolabeled MECA-79 antibody in the transplanted heart, wherein the presence of radiolabeled MECA-79 in the transplanted heart is indicative of chronic allograft rejection.

* * * * *